(12) United States Patent
Maggio et al.

(10) Patent No.: US 10,569,410 B2
(45) Date of Patent: Feb. 25, 2020

(54) DEVICE FOR STABILIZING AND SECURING TESTING TUBES IN CAST-IN-DRILLED-HOLE PILES

(71) Applicants: Michael Maggio, San Dimas, CA (US); William Burton, Goodyear, AZ (US)

(72) Inventors: Michael Maggio, San Dimas, CA (US); William Burton, Goodyear, AZ (US)

(*) Notice: Subject to any disclaimer, the term of this patent is extended or adjusted under 35 U.S.C. 154(b) by 0 days.

(21) Appl. No.: 16/253,780

(22) Filed: Jan. 22, 2019

(65) Prior Publication Data

US 2019/0168373 A1 Jun. 6, 2019

Related U.S. Application Data

(62) Division of application No. 15/614,951, filed on Jun. 6, 2017, now Pat. No. 10,220,503.

(51) Int. Cl.
*B25H 1/00* (2006.01)
*G01N 33/38* (2006.01)
*G01H 1/04* (2006.01)

(52) U.S. Cl.
CPC .............. *B25H 1/0042* (2013.01); *G01H 1/04* (2013.01); *G01N 33/383* (2013.01)

(58) Field of Classification Search
CPC .... G01N 33/383; G01N 33/42; B25H 1/0042; B25H 1/04; E21B 49/00; E21D 5/06; G01V 1/00
See application file for complete search history.

(56) References Cited

U.S. PATENT DOCUMENTS

| | | | |
|---|---|---|---|
| 6,301,551 B1 | 10/2001 | Piscalko | |
| 6,783,273 B1 | 8/2004 | Mullins | |
| 7,007,620 B2 | 3/2006 | Veazey | |
| 9,074,473 B2 | 7/2015 | Alter | |
| 2012/0012470 A1 | 1/2012 | Bartholomew | |
| 2012/0314540 A1* | 12/2012 | Alter | E21D 5/06 367/86 |
| 2015/0233230 A1* | 8/2015 | Likins, Jr. | E02D 1/02 166/254.1 |

* cited by examiner

*Primary Examiner* — Suman K Nath
(74) *Attorney, Agent, or Firm* — Flyer & Flyer, a Professional Law Corporation; David R. Flyer

(57) ABSTRACT

Concrete which is used in structural support of freeways, bridges, and large buildings, must be tested for anomalies. The testing equipment consists of probes which are inserted into testing tubes. The tubes are placed within rebar cages before concrete is poured. The prior art involved ad hoc methods of tying the tubes to the rebar. The improvement is pre-fabricated, mass produced cylindrical devices which can be axially snapped onto the testing tube. A first cylindrical device also has a perpendicular receptacle which facilitates connection to a second cylindrical device, where the second device can be axially snapped onto a piece of longitudinal rebar on the edge of the rebar cage. The combined first and second devices safely, accurately, and quickly affix the testing tubes to the rebar.

7 Claims, 6 Drawing Sheets

DEVICE FOR STABILIZING AND SECURING TESTING TUBES IN CAST-IN-DRILLED-HOLE PILES

CROSS-REFERENCE

This is divisional application of Ser. No. 15/614,951.

STATEMENT REGARDING FEDERAL SPONSORED RESEARCH

None.

PARTIES TO JOINT RESEARCH AGREEMENT

None.

BACKGROUND OF THE INVENTION

Structural support for freeways, bridges and large buildings usually requires placement of a series of concrete piles, where pile is defined as a slender, deep foundation unit, entirely or partially embedded in the ground. The concrete pile is reinforced by a steel cage of rebar. The purpose of the pile is to transfer heavy axial or lateral loads to a deep stratum below the ground surface. To test the quality of the concrete piles, testing tubes with testing probes are inserted prior to the pour of concrete. The prior art involved ad hoc methods for securing the testing tubes to the rebar cage. Our improvement on the prior art involves uniform method for quickly and safely snapping a first pre-formed device onto each of the tubes, connecting the first device to a second pre-formed device, which second device is then snapped onto the rebar.

One common pile design is referred to as Cast-in-Drilled-Hole (CIDH). The CIDH pile is a cylindrical shaft at least two feet in diameter, with a length necessary to accommodate the particular needs of a construction project which length could be substantially greater than 30 feet.

The first step in placement of the CIDH pile is to drill a hole in the ground. After the hole is drilled, the second step involves building a cylindrical rebar ("reinforcing bar") cage or steel skeleton to provide reinforcement for later to be poured concrete. The third step is to insert hollow PVC or iron or metal alloy testing tubes into the cage. The purpose of the tubes is to accommodate testing probes which are used to measure the quality of the concrete pour. The fourth step is to affix the tubes to the cage so that the tubes remain in designated positions during the concrete pour. The fifth step is to place the cage with the tubes into the hole. The sixth step is to pour concrete into the hole. The final, seventh step involves insertion of Cross-hole Sonic Logging (CSL) or Gamma-Gamma Logging (GGL) testing probes into the tubes. The CSL or GGL are used to detect anomalies or defects in the poured concrete.

The prior art construction techniques involved affixing the testing tubes to the rebar cage by use of baling wire or other unspecified, ad hoc coupling techniques. See for instance, Alter U.S. Pat. No. 9,074,473 (Jul. 7, 2015) which relied on hollow rebar tubes to house the CSL or GGL probes: "hollow rebar may provide continuous access tube segments that can be coupled to any required length, and the couplings may be watertight with rubber seals to prevent leakage," (3:54-57). The coupling of tubes and rebar was only vaguely identified, except to acknowledge the necessity of watertight couplings.

Prior art recognized that the tubes must be positioned in a circle at designated intervals, parallel to the longitudinal axis of the drilled shaft to insure complete coverage for testing the concrete within the shaft. Whether the testing method involved sound echo, radiation or temperature changes to detect anomalies, pre-positioning of the tubes is important to make sure there are no gaps in coverage. See for example, Mullins U.S. Pat. No. 6,783,273 (Aug. 31, 2004): "The spacing and number of logging tubes is selected such that the frequency of tubes provides sufficient information to detect defects within both the core and the protective cover," (2:22-24).

The testing tubes have uniform outer diameters for use in CIDH piles, for instance 2¼". This uniform diameter feature accommodates a prefabricated, mass produced device for securing and stabilizing testing tubes (hereafter "securing device") within the rebar cages in CIDH piles. The securing device can be quickly and safely affixed to the testing tubes.

Similarly, rebar have uniform outer diameters for use in CIDH piles, typically ranging from ½" to ⅞" diameter. Once again, the uniform diameter feature accommodates a prefabricated, mass produced device for attachment to the longitudinal rebar, within the rebar cages in CIDH piles.

The need for complete coverage in the placement of testing tubes to insure sufficient information about the concrete can be obtained after the pour, along with the need to quickly and safely insert the tubes within the rebar cage, and to tie the tubes to the cage can be met by prefabricated devices which easily snap onto the tubes or slide onto the tubes, where the devices can be connected to one another, and then the devices can be snapped onto and be tied to a longitudinal piece of rebar in the cage.

BRIEF DESCRIPTION OF DRAWINGS

There are two views.

There are two side views of different embodiments of the device, at two locations.

There are two overhead views of two embodiments of the device.

There are three views.

DETAILED DESCRIPTION OF VARIOUS EMBODIMENTS

Figure 2:
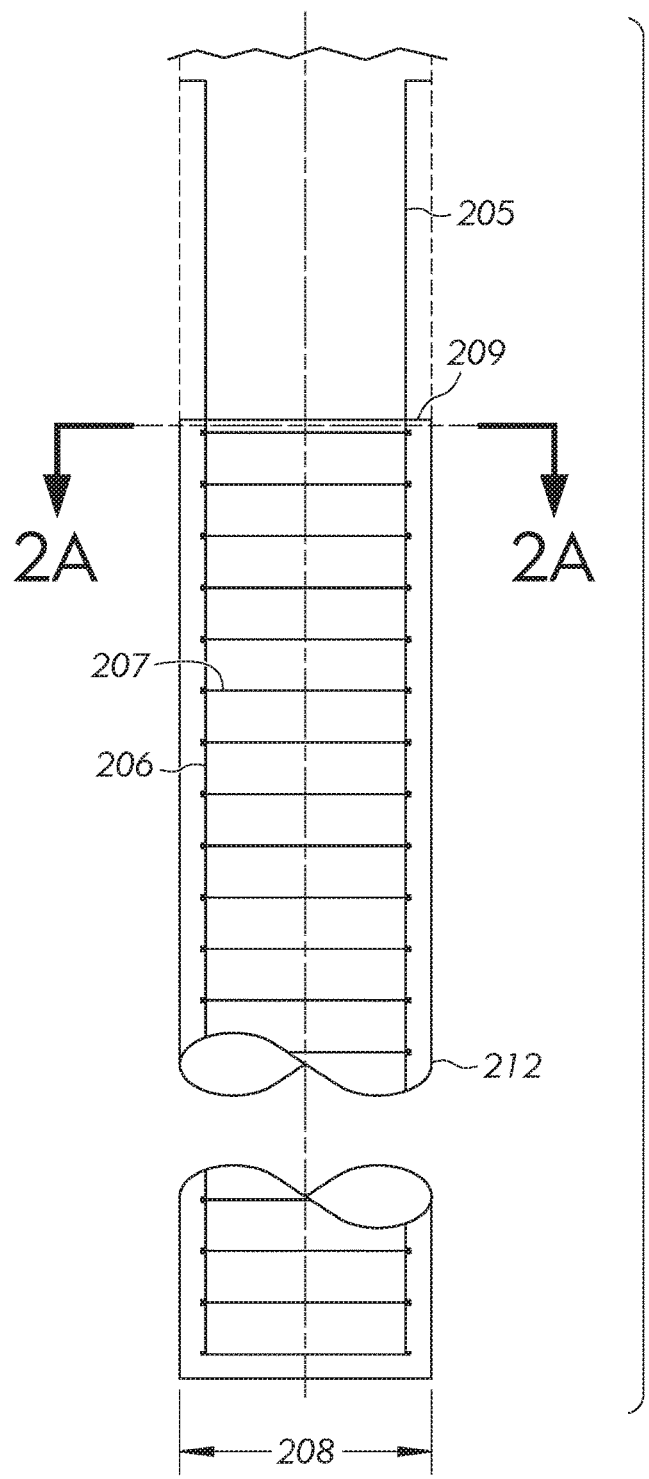
FIG. 2 is a side view of the rebar cage for the CIDH pile.
Figure 2A:
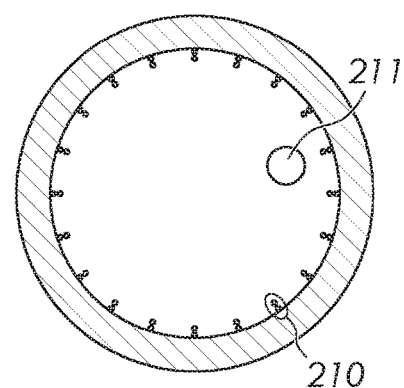
FIG. 2A is a cross-sectional view showing the prior art.

FIG. 2A shows the prior art method of affixing testing tubes to a rebar cage 205. The cage is constructed of rebar, with some members running in a longitudinal 206 direction, tied together by other members running in a latitudinal 207 direction. The longitudinal 206 rebar members run the length of the cage, from top 209 to bottom 208, where bottom is at the deepest part of the hole. The outline of a hole into which the rebar cage will be inserted, is shown at 212. Due to the extreme length of the cage, latitudinal 207 rebar elements are tied to the longitudinal 206 rebar elements for support. At the top of the cage 209, the cross-sectional view at FIG. 2A shows how wires 210 were extended from the cage and wrapped around the hollow testing tubes 211. The testing tubes 211 are constructed of hollow PVC, other synthetic plastic polymers, iron rebar or other metal alloys.

The disadvantages of the prior art included: inaccuracy in placement of testing tubes because each wire tie was of a different length, meaning that the tubes were not equidistantly located from the circumference of the rebar cage; involvement of significant time related to a labor intensive method of tying the wires to the tubes; and, danger to the workmen who had to insert hands and arms into the rebar cage to secure the tubes.

Figure 1A:
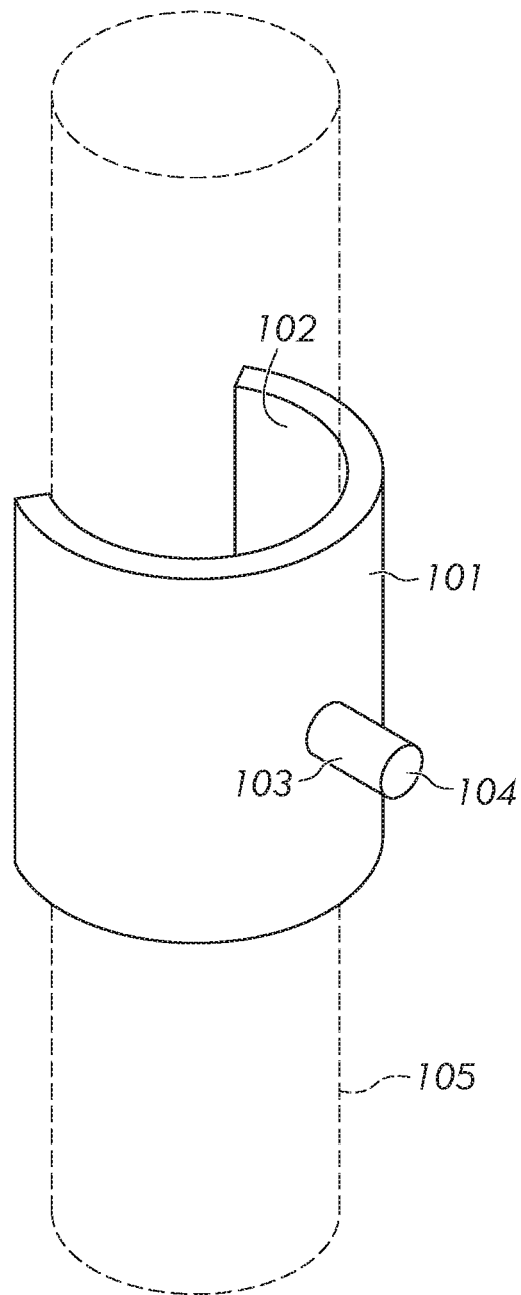
FIG. 1A is a perspective view of an embodiment of the device for securing and stabilizing testing tubes in a Cast-in-Drilled-Hole (CIDH) pile.
Figure 1B:
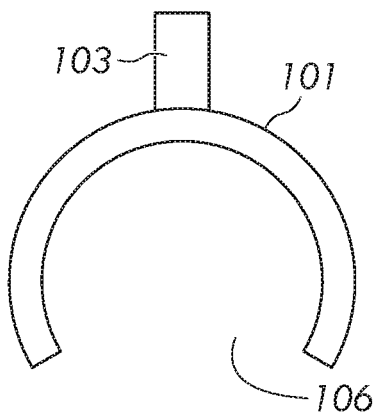
FIG. 1B, is a top view of the device.

A first device for stabilizing and securing hollow testing tubes ("securing device") is shown in FIG. 1A. In the depicted embodiment of FIG. 1A, the securing device is a hollow, cylinder with a cut of approximately one-third of its diameter running its axial length 101 and with an inside diameter slightly larger than an outside diameter of a testing tube 105. The securing device is pre-formed, so each device is of uniform dimensions. The cylinder's inner diameter 102 is slightly larger than the outer diameter of the testing tube 105, so that the cylinder can be axially snapped onto the testing tube 105, in one quick motion. The cylinder 101 also has a protruding knob 103 which is perpendicular to the cylinder's axis, so that the cylinder 101 can be inserted into a connector piece at 104, to permit attachment to the rebar cage. A top view in FIG. 1B, shows the relative positions on the cylinder 101 of the protruding knob 103 and the cut 106. The connector piece is shown in FIG. 6C, at 607. On one side of the connector piece, a hole 608 accommodates the knob 103, which knob is snugly pressed into the hole.

Figure 6A:
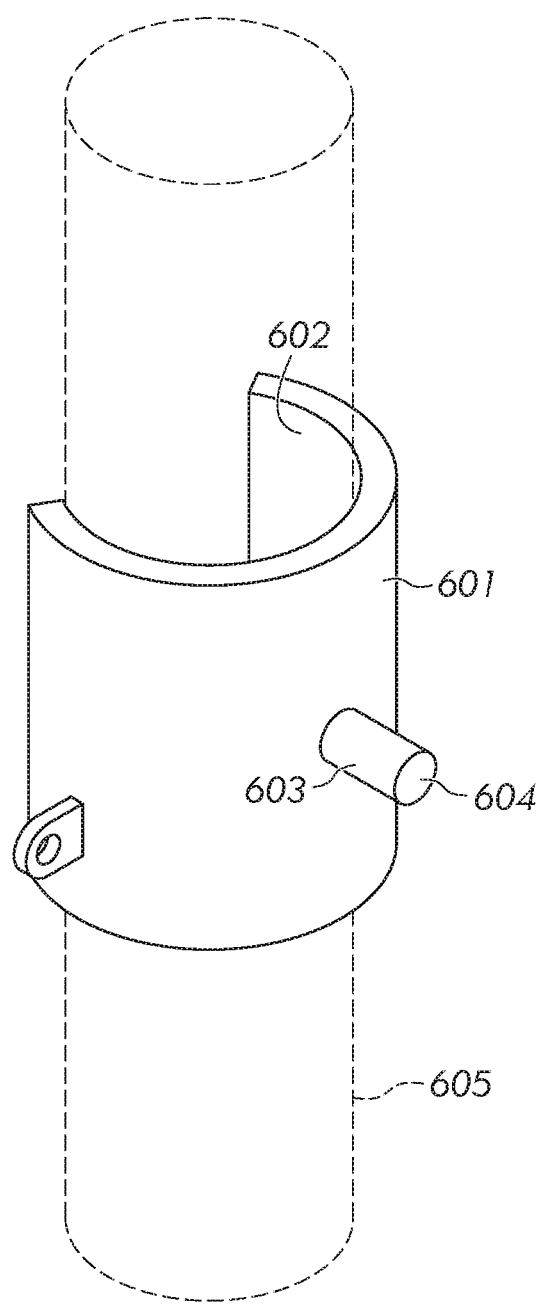
FIG. 6A, is a perspective view of an embodiment of the device for attaching to rebar.
Figure 6B:
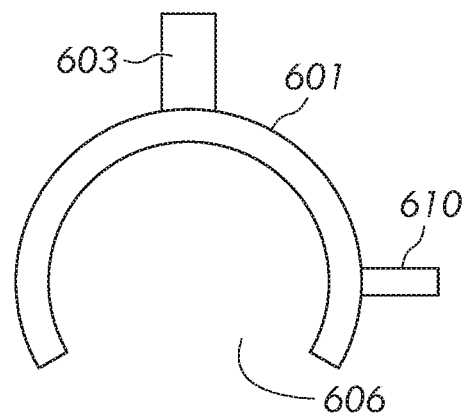
FIG. 6B, is a top view of the device.
Figure 6C:
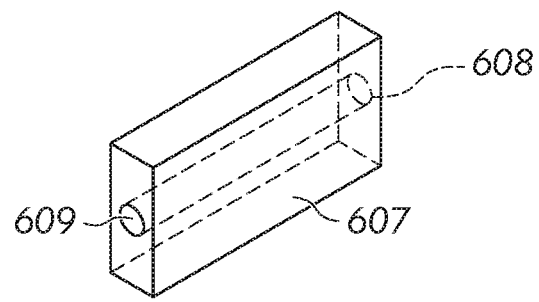
FIG. 6C, is a perspective view of the connector between two devices.

A second device for attaching the first device to longitudinal rebar in the cage ("attaching device") is shown in FIG. 6A. In the depicted embodiment at FIG. 6A, the attaching device is a hollow, cylinder with a cut of approximately one-third of its diameter running its axial length 601 and with an inside diameter slightly larger than an outside diameter of a longitudinal rebar 605. The attaching device is pre-formed, so each device is of uniform dimensions. The cylinder's inner diameter 602 is slightly larger than the outer diameter of the rebar 605, so that the cylinder can be axially snapped onto the rebar 605, in one quick motion. The cylinder 601 also has a protruding knob 603 which is perpendicular to the cylinder's axis, so that the cylinder 601 can be inserted into a connector piece at 604, to permit attachment to the rebar cage. A top view in FIG. 6B, shows the relative positions on the second device 601 of the protruding knob 603, the tab 610 and the cut 606. The connector piece is shown in FIG. 6C, at 607. On one side of the connector piece, a hole 609 accommodates the knob 603, which knob is snugly pressed into the hole.

Figure 3A:
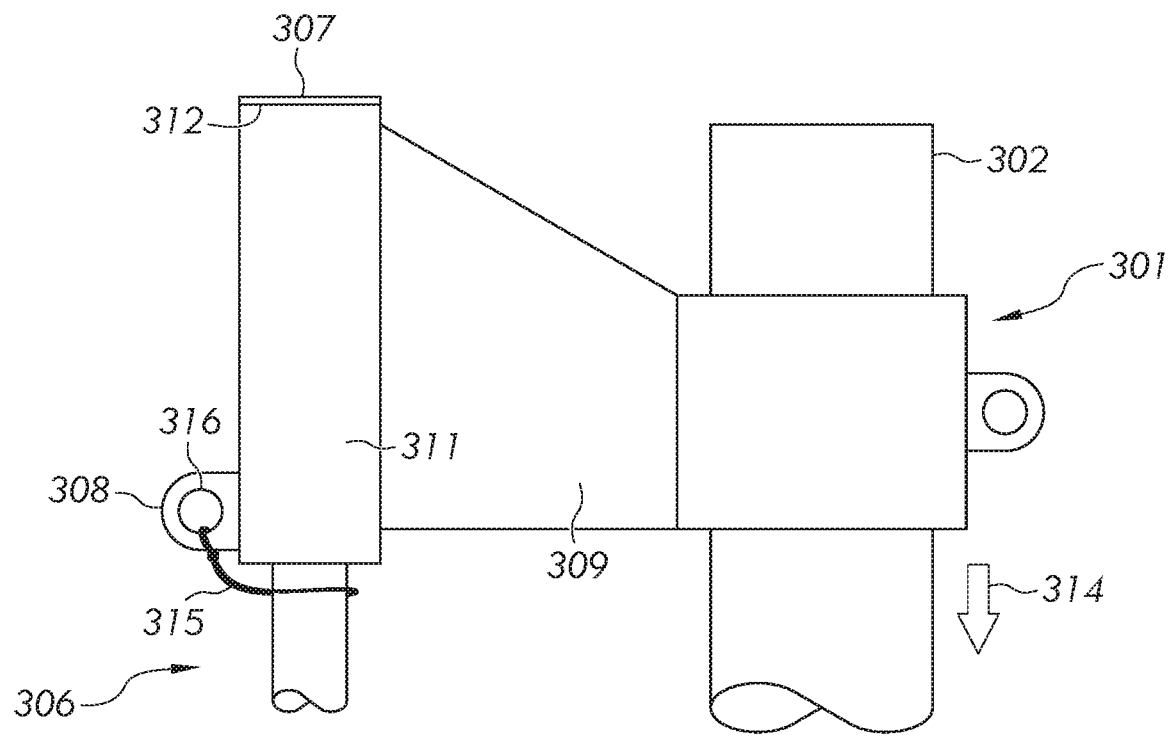
in FIG. 3A, a first embodiment of the device is shown at the top of the rebar cage; and, in FIG. 3B, a second embodiment of the device is shown at a designated distance from the top of the cage.
Figure 3B:
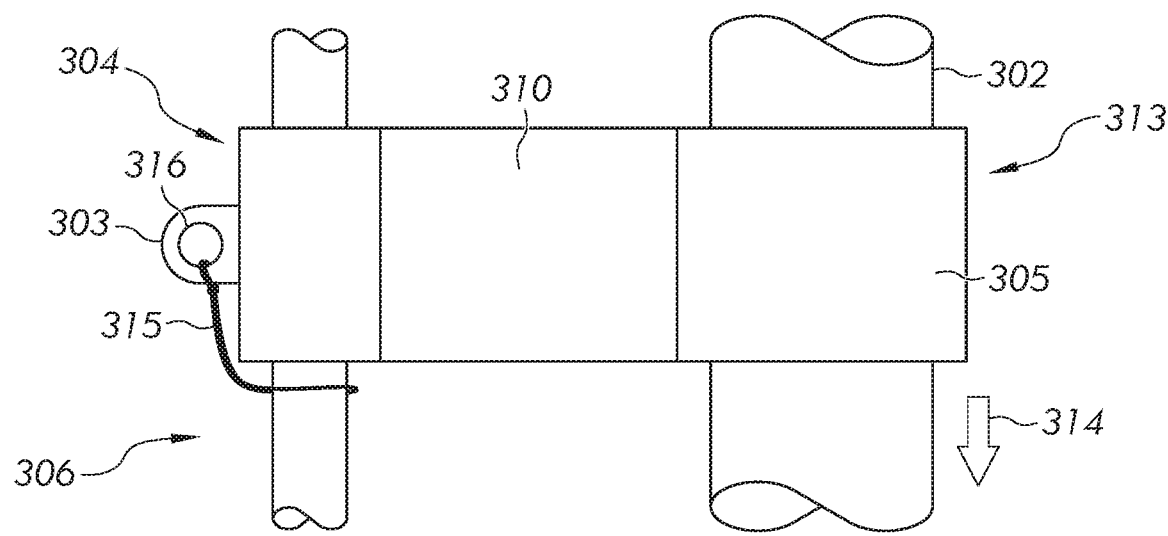

FIG. 3A and FIG. 3B show two embodiments of another securing device. Rather than snap onto the testing tube 302, the securing device 301 is a hollow cylinder without a cut, which is slid onto the tube from an end of the tube that is to be inserted into the rebar cage 314, and which end will later be nearest to the bottom of the hole in the ground, from FIG. 2 at 208. In FIG. 3A, a first hollow, cylinder without a cut 301, is shown attached to the testing tube 302. In sequence, several of the first cylinders 301 are slid onto the tube 302 from the same direction and equally spaced from one another, for the entire length of the tube. A trapezoid connector 309 joins each of the first cylinders 301 on the tube 302 to each of a second cylinder, previously referred to as the attaching device, with a cut of approximately one-third of its diameter running its axial length 311, where the second cylinder has a tab 308, and the tab has a centering hole 316. The trapezoid connector 309 is selected in this embodiment, because its added thickness will promote greater stability. In another embodiment, the trapezoid connector 309 is used only for the connection at the top of the rebar cage 307. The second cylinder 311 which is at a top of the cage 307 is snapped onto a longitudinal rebar 306 and secured in place by a cap 312 which rests on top of the rebar 306. The top attaching device can also be tied by zip ties 315 through the hole 316 and to the rebar.

At a designated distance from the top of the rebar cage 307, a second cylinder 311 with a tab 308 that has a hole 316, is snapped onto the longitudinal rebar 306, and secured in place by a zip tie 315. In sequence, for the entire length of the longitudinal 306 rebar, each of the second cylinders 311 with the tabs 308 is snapped onto the longitudinal rebar 306, and secured in place by zip ties 315 through the hole 316 and to the rebar.

In another embodiment, depicted in FIG. 3B, a first hollow, cylinder 305 with an inner diameter which is slightly larger than an outer diameter of the testing tube 302, is shown connected to the tube. The first cylinder 305 is slid onto the testing tube 302 from an end of the tube which is first inserted into the rebar cage 314. In sequence, several of the first cylinders 305 are slid onto the tube 302 from the same direction, and equally spaced from one another, for the entire length of the tube 302. A rectangular connector 310 joins the first cylinder 305 to a second cylinder 304. The second cylinder 304 has a tab 303 with a centering hole 316 so that it can be secured by zip ties 315, to the longitudinal rebar 306. In sequence, each of the second cylinders 311 with tabs 303 are secured by zip ties 315 through the hole and to the rebar 306.

Figure 4A:
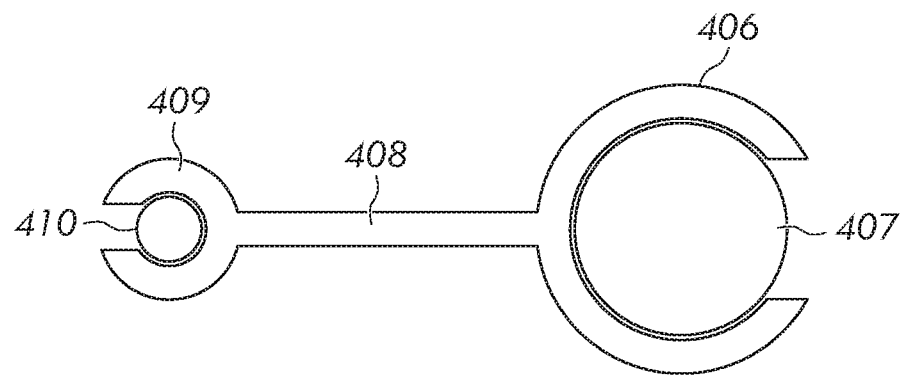
in FIG. 4A, a first coupled device which allows opposing side access is shown.
Figure 4B:
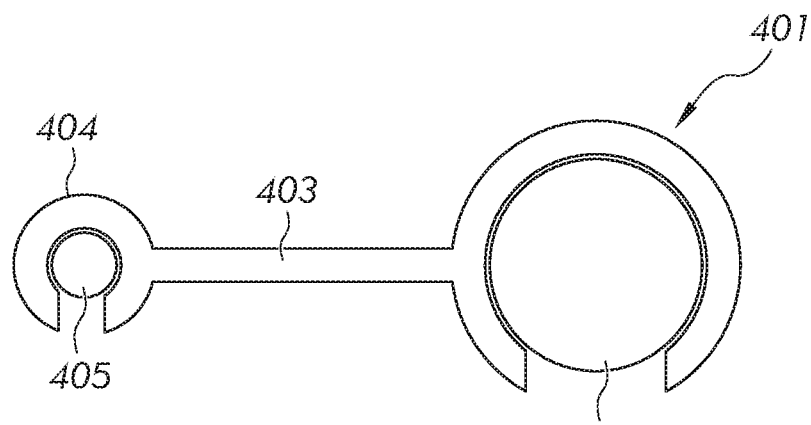
in FIG. 4B, a second coupled device which allows same side access is shown.

FIG. 4A and FIG. 4B show two embodiments of another securing device. In FIG. 4A, a first hollow cylinder with a cut of approximately one-third of its diameter running its axial length 406 allows opposing side access to snap onto a testing tube 407. A connector 408 joins the first cylinder 406 to a second hollow cylinder with a cut of approximately one-third of its diameter running its axial length 409. The second cylinder 409 also allows opposing side access to snap onto the longitudinal rebar 410.

In FIG. 4 B, a first hollow cylinder with a cut of approximately one-third of its diameter running its axial length 401 and with an inner diameter which is slightly larger than the outer diameter of a testing tube, allows same side access to snap onto the testing tube 402. A connector 403 joins the first cylinder 401 to a second hollow cylinder with a cut of approximately one-third of its diameter running its axial length 404 and with an inner diameter which is slightly larger than the outer diameter of longitudinal rebar. The second cylinder 404 also allows same side access to snap onto the rebar 405.

Figure 5:
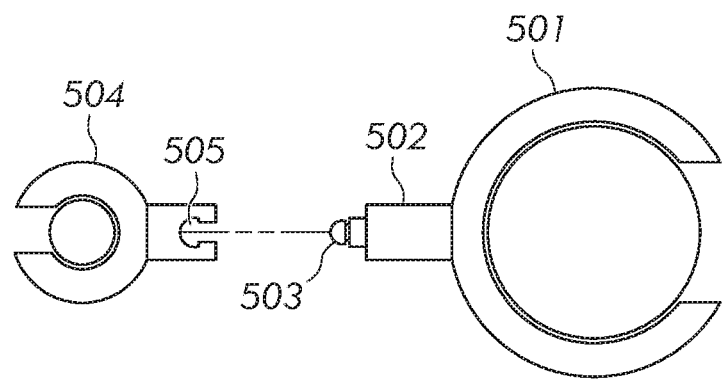
FIG. 5 shows an overhead view of another embodiment of the device with a swivel connector.

In FIG. 5 another embodiment of a securing device is shown. A first hollow cylinder with a cut of approximately one-third of its diameter running its axial length 501 and with an inner diameter which is slightly larger than the outer diameter of a testing tube is shown. The first cylinder can be snapped onto the testing tube as previously descried. The first cylinder 501 has a protruding male receptacle 502 which is perpendicular to the cylinder's axis. A ball 503 is embedded in the receptacle 502 at an end farthest from the cylinder 501. The ball 503 permits a connection with a second hollow cylinder with a cut of approximately one-third of its diameter running its axial length 504 and with an inner diameter which is slightly larger than the outer diameter of longitudinal rebar, to swivel. The second cylinder 504 has a female receptacle 505 which accepts the ball 503 from the first cylinder 501. Then the second cylinder is snapped onto the rebar.

A method for stabilizing and securing logging tubes in Cast-In-Drilled-Hole piles, comprising: Drilling a hole in the ground, the outline of a hole is shown in FIG. 2, at 212. After the hole is drilled, the second step involves building a cylindrical rebar cage or steel skeleton, shown in FIG. 2, at 205, to provide reinforcement for later to be poured concrete. The third step is to insert hollow PVC or iron or metal alloy testing tubes into the cage, shown in FIG. 2A, the cross-section at 211. The purpose of the tubes is to accommodate testing probes which are used to measure the quality of the concrete pour. The fourth step is to affix the tubes, by a securing device which is the improvement as shown in FIG. 1A at 101, to the cage so that the tubes remain in designated positions during the concrete pour. The tubes shown in FIG. 3A, at 302, run longitudinally. A first hollow device with a cut of approximately one-third of its diameter running its axial length 301 is snapped onto the tube 302. Then in sequence, several first devices 301 are snapped onto the tube 302, and equally spaced for the length of the tube. A connector 309 joins the first device 301 with a second hollow device with a cut of approximately one-third of its diameter running its axial length 311. The second device 601, from FIG. 6A, is snapped on the rebar 605. Then in sequence, several second devices 601 are snapped on the rebar 605, and equally spaced for the length of the rebar. Returning to FIG. 3A, the second devices will also be secured to the rebar by zip ties 315 through a centering hole 316 in a tab 308 attached to the device 311. The fifth step is to place the cage 205 in FIG. 2 with the now secured tubes 211 in FIG. 2A into the hole 212 in FIG. 2. The sixth step is to pour concrete into the hole. The final, seventh step involves insertion of Cross-hole Sonic Logging (CSL) or Gamma-Gamma Logging (GGL) testing probes into the tubes. The CSL or GGL are used to detect anomalies or defects in the poured concrete.

A method for stabilizing and securing logging tubes in Cast-In-Drilled-Hole piles, comprises: Drilling a hole in the ground, the outline of a hole is shown in FIG. 2, at 212. After the hole is drilled, the second step involves building a cylindrical rebar cage or steel skeleton, shown in FIG. 2 at 205, to provide reinforcement for later to be poured concrete. The third step is to insert hollow PVC or iron or metal alloy testing tubes into the cage, shown in FIG. 2A at 211. The purpose of the tubes is to accommodate testing probes which are used to measure the quality of the concrete pour. The fourth step is to affix the tubes to the cage so that the tubes remain in designated positions during the concrete pour. The tubes shown in FIG. 3A, at 302, run longitudinally. A first hollow cylinder without a cut 301 is slid onto the tube 302. Then in sequence, each of several first cylinders 301 are slid onto the tube 302, and equally spaced for the entire length of the tube. A connector 309 joins the first device 301 with a second hollow device with a cut of approximately one-third of its diameter running its axial length 311. The second device 601, from FIG. 6A, is snapped on the rebar 605. Then in sequence, several second devices 601 are snapped on the rebar 605, and equally spaced for the length of the rebar. Returning to FIG. 3A, the second devices will also be secured to the rebar by zip ties 315 through a centering hole 316 in a tab 308 attached to the device 311. The fifth step is to place the cage 205 with the now secured tubes 211 into the hole 212. The sixth step is to pour concrete into the hole. The final, seventh step involves insertion of Cross-hole Sonic Logging (CSL) or Gamma-Gamma Logging (GGL) testing probes into the tubes. The CSL or GGL are used to detect anomalies or defects in the poured concrete.

The pre-formed semi-cylinder device can be prefabricated PVC or other synthetic plastic polymer, or rubber, so that it is rigid to prevent movement, but somewhat flexible to permit snapping onto either a testing tube or onto a piece of rebar.

Various embodiments described above may be combined with each other in connection with the claimed device. Further, the order of steps in the claimed method may be changed. Other embodiments of the invention will be apparent to a person of ordinary skill in the art. It is intended that the specification and embodiments be considered as exemplary only.

We claim:

1. A device for stabilizing and securing testing tubes, which are used for insertion of testing probes into cast-in-drilled hole piles (CIDH), comprising:
    a first pre-formed, hollow cylinder with a cut of approximately one-third of its diameter running its axial length, with a first protruding knob that is perpendicular to its axial length, and with an inner diameter that is slightly larger than an outer diameter of a testing tube, so that the first hollow cylinder is configured to axially snap onto the testing tube in one quick motion;
    a second pre-formed, hollow cylinder with a cut of approximately one-third of its diameter running its axial length, with a second protruding knob that is perpendicular to its axial length, with a tab having a hole where the tab is located approximately 90 degrees away from the knob on an outer diameter of the cylinder, and with an inner diameter of the cylinder which is slightly larger than an outer diameter of a longitudinal rebar located on an edge of a rebar cage, so that the second hollow cylinder is configured to axially snap onto the longitudinal rebar, where the rebar cage is used to reinforce concrete that is later to be poured;
    a connector which has two holes to permit insertion of the protruding knobs from each of the first hollow cylinder and the second hollow cylinder;
    where the first protruding knob of the first hollow cylinder is inserted into the connector;
    where the second protruding knob of the second hollow cylinder is inserted into the connector; and,
    where the second hollow cylinder is axially snapped onto the rebar and then tied in place by zip ties through the hole in the tab and around the rebar to secure the testing tube to the rebar.

2. The device of claim 1, where the first hollow cylinder and the second hollow cylinder respectively connect to the testing tube and the rebar on opposing sides.

3. The device of claim 1, where the first hollow cylinder and the second hollow cylinder respectively connect to the testing tube and the rebar on the same sides.

4. A device for stabilizing and securing testing tubes, which are used for insertion of testing probes in cast-in-drilled-hole piles, comprising:
    a first pre-formed, hollow cylinder without a cut, with a first protruding knob that is perpendicular to its axial length, and with an inner diameter slightly larger than an outer diameter of a testing tube, so that the first hollow cylinder is configured to axially snap onto the testing tube in one quick motion;

a second pre-formed, hollow cylinder with a cut of approximately one-third of its diameter running its axial length, with a second protruding knob that is perpendicular to its axial length, with a tab having a hole where the tab is located approximately 90 degrees away from the knob on an outer diameter of the cylinder, and with an inner diameter of the cylinder which is slightly larger than an outer diameter of a longitudinal rebar located on an edge of a rebar cage, so that the second hollow cylinder is configured to axially snap onto the longitudinal rebar, where the rebar cage is used to reinforce concrete that is later to be poured;

a connector which has two holes to permit insertion of the protruding knobs from each of the first hollow cylinder and the second hollow cylinder;

where the first hollow cylinder is slid onto the testing tube from an end of the testing tube which is to be nearest to a bottom of a hole in the ground into which the rebar cage will be installed;

where the first protruding knob of the first hollow cylinder is inserted into the connector;

where the second protruding knob of the second hollow cylinder is inserted into the connector; and, where the second hollow cylinder is axially snapped onto the rebar and then tied in place by zip ties through the hole in the tab and around the rebar to secure the testing tube to the rebar.

5. The device of claim 4, where the first hollow cylinder and the second hollow cylinder respectively connect to the testing tube and the rebar on opposing sides.

6. The device of claim 4, where the first hollow cylinder and the second hollow cylinder respectively connect to the testing tube and the rebar on the same sides.

7. A device for stabilizing and securing testing tubes, which are used for insertion of testing probes in cast-in-drilled hole piles, comprising:

a first hollow, cylinder with a cut of approximately one-third of its diameter running its axial length, and with an inner diameter that is slightly larger than an outer diameter of a testing tube, so that the first hollow cylinder is configured to axially snap onto the testing tube in one quick motion; and where the first hollow cylinder has a protruding male receptacle which is perpendicular to the cylinder's axis and into which receptacle a ball is embedded;

a second pre-formed, hollow cylinder with a cut of approximately one-third of its diameter running its axial length, with a tab having a hole, and with an inner diameter of the cylinder which is slightly larger than an outer diameter of a longitudinal rebar located on an edge of a rebar cage, so that the second hollow cylinder is configured to axially snap onto the longitudinal rebar, where the rebar cage is used to reinforce concrete that is later to be poured;

where the second hollow cylinder has a female receptacle which is capable of accepting the ball from the first hollow cylinder;

where the female receptacle of the second hollow cylinder is snuggly pressed onto the ball of the first hollow cylinder, such that the ball permits a swiveling connection between the first hollow cylinder and the second hollow cylinder; and, where the second hollow cylinder is axially snapped onto the rebar and then tied in place by zip ties through the hole in the tab and around the rebar to secure the testing tube to the rebar.

\* \* \* \* \*